United States Patent [19]

Riseman

[11] 4,321,544

[45] Mar. 23, 1982

[54] METHOD AND IMPROVED APPARATUS FOR OBTAINING TEMPERATURE-CORRECTED READINGS OF ION LEVELS AND READINGS OF SOLUTION TEMPERATURE

[76] Inventor: John H. Riseman, 6 Holly Ave., Cambridge, Mass. 02138

[21] Appl. No.: 122,001

[22] Filed: Feb. 19, 1980

[51] Int. Cl.³ .............................................. G01N 27/42
[52] U.S. Cl. ................................................... 324/438
[58] Field of Search ................ 324/438, 441, 468, 453

[56] References Cited

U.S. PATENT DOCUMENTS

| Re. 27,668 | 6/1973 | Soltz et al. | 324/438 |
|---|---|---|---|
| 2,674,719 | 4/1954 | Williams, Jr. | 324/438 |
| 3,405,048 | 10/1968 | Soltz | 324/438 |
| 3,806,797 | 4/1974 | Harvey | 324/438 |
| 4,196,383 | 4/1980 | Teass, Jr. | 324/438 |

Primary Examiner—Michael J. Tokar

[57] ABSTRACT

An improved temperature-compensated ion measurement method and apparatus for use therein. The method comprises placing a probe in a solution whose ion level (for example, pH) is to be measured and measuring the A.C. resistance of the probe in a manner that does not adversely affect the simultaneous measurement of the probe's D.C. potential, and then driving from these two measurements the ion level of the solution corrected for its temperature.

17 Claims, 1 Drawing Figure

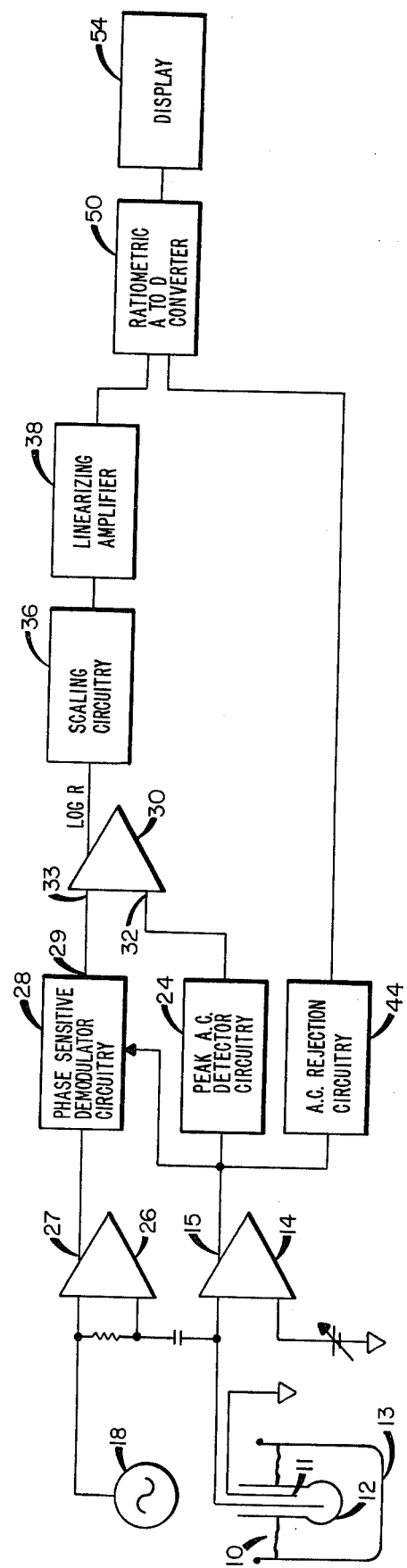

METHOD AND IMPROVED APPARATUS FOR OBTAINING TEMPERATURE-CORRECTED READINGS OF ION LEVELS AND READINGS OF SOLUTION TEMPERATURE

BACKGROUND OF THE INVENTION

1. Field of the Invention

The present invention relates generally to the measurement of ions in solution and more particularly to an improved temperature-compensated ion measurement method with use with a direct readout ion meter (for example, a pH meter) and an improved device for obtaining temperature-compensated readings of on levels in test solutions.

2. The Prior Art

Devices that measure the ion levels (activity or concentration) of solutions are essentially voltmeters that measure the D.C. potential between a sensing and a reference electrode placed in such solutions. Glass sodium electrodes, for example, are used to sense the ion levels of sodium in solutions. Glass membrane electrodes are used to sense the pH of certain solutions containing hydrogen ion. For purposes of convenience, the present invention will be described in terms of pH measurement, it being understood that those skilled in the art will realize how measurements of other ions or measurements using membranes other than glass can be made in accord with the teachings of this disclosure.

A pH meter is a voltmeter that measures the D.C. potential between a glass membrane pH electrode and a reference electrode and scales that measurement into pH values. Generally, the sensing and reference electrodes are combined into a single unit, or pH probe. When a pH probe is placed in a solution, an exchange equilibrium is established between hydrogen ions in the solution and ions in the glass pH sensitive membrane. This equilibrium is the source of the D.C. potential that is measured. The reference electrode supplies a known and stable reference potential against which the D.C. potential of the membrane may be measured. The difference between the glass electrode potential and the reference electrode potential varies in a manner known from the Nernst equation. That potential difference is a function of hydrogen ion activity and the "slope factor" (typically measured in units of millivolts per pH unit), which varies with temperature according to the Nernst equation. For example, at 0 degrees Centigrade, the slope is 54.196; at 30 degrees Centigrade, it is 60.148; at 60 degrees Centigrade, it is 66.100; at 100 degrees Centigrade, it is 74.036 (see Westcott, *pH Measurements* [New York: Academic Press, 1978], pages 25 and 148). Some pH meters of early design were provided with multiple scales to permit pH values to be read directly at several different temperatures. Most present day laboratory pH meters, however, are equipped to give both manual and automatic temperature compensation.

Automatic temperature compensation is normally accomplished through the use of a separate temperature probe (usually a resistance thermometer) mounted next to the pH (or sensing) probe. Both probes are simultaneously placed in the sample solution. At any given temperature, the sensing probe produces a voltage value related to the pH of the test solution. With varying temperature, this value must be scaled in accordance with the temperature of the test solution. The temperature probe either modifies the gain of an amplifier or changes the potential at the ratiometric input of an analog-to-digital converter, ultimately to produce a temperature-corrected pH reading.

The use of two probes, however, to accomplish automatic temperature compensation is cumbersome and inconvenient, especially where sample size is small or where sample carryover by the probes can reduce the accuracy of the results. In the past, this problem has been addressed by building the resistance thermometer into the pH sensing probe. This solution to the problem, however, results in expensive pH probe initial cost and also in expensive operating costs because the thermocompensator must be discarded if part of the probe fails for any reason. A further complication arises because the thermal response characteristics as a function of time typically differ for the pH sensing probe and the temperature probe. As a consequence, care must be exercised to be sure that both devices have reached temperature equilibrium so that erroneous readings will not be obtained.

An electrode characteristic also known to those acquainted with the state of the art is that the log of the pH glass membrane resistance varies inversely with the absolute temperature of the solution. This fact, however, has heretofore not been put to any practical use.

SUMMARY OF THE INVENTION

The apparatus of the present invention comprises in combination a conventional pH sensing probe (or other ion probe), conventional circuitry for amplifying and displaying the pH value, circuitry that applies an A.C. signal to the pH sensing probe, circuitry that interprets the resulting A.C. signal in terms of probe A.C. resistance, and circuitry that transforms this resistance information into a temperature correction signal that is applied to the conventional pH measuring circuitry so as to provide temperature-corrected pH readings.

Furthermore, the apparatus of the present invention can provide direct readings of solution temperature without the need for a separate temperature probe or temperature sensing element.

The apparatus of the present invention, used in accord with the method of the present invention, provides an improvement over prior art means for obtaining temperature-compensated pH readings.

It is, therefore, a principal object of the present invention to provide an improved method for obtaining temperature-compensated pH readings and temperature readings while eliminating the need for placing a separate temperature probe in the test solution in addition to the pH probe itself.

It is also an object of the present invention to provide an improved combined pH and temperature measurement technique that uses the A.C. resistance of the glass membrane itself to provide information concerning the actual membrane temperature so that accurate automatic pH temperature compensation is obtained.

It is a further object of the present invention to provide an improved combined pH and temperature measurement technique that requires smaller solution volume to make more precise and accurate readings than is possible with presently available temperature-compensated pH measuring techniques.

Typically, the form the invention takes is an improved pH meter incorporating additional circuits not found in conventional pH meters and used in accord with a method comprising: placing a pH probe in a solution while inducing an A.C. signal across the probe;

measuring the average D.C. potential of the probe; converting the amplitude of the induced A.C. signal to a D.C. potential (V); taking the log of V; measuring the A.C. current in phase with the signal across the probe; converting the in-phase current to a D.C. potential proportional to the current (I); taking the log of I; finding the log of the probe resistance (log R) by subtracting log I from log V; taking the reciprocal of log R; scaling that reciprocal to obtain the solution temperature; and using such temperature information to modify the scaling factor used to convert the probe potential into a pH reading corrected for solution temperature.

To better understand the invention, consider the properties of the typical pH probe. Typically, the resistance of the pH glass membrane at D.C. and at low frequency A.C. at room temperature is in the range of 100 to 1000 megohms. The present invention arises in part from the surprising finding that all pH electrodes tested exhibit almost identical changes in electrical resistance as a function of temperature. The resistance decreases by a factor of 2 for every 9 to 10 degrees Centigrade increase in solution temperature. This observation means that electrodes of different design and manufacture can readily be substituted one for another so long as a scaling factor is applied to compensate for the resistance differences from electrode to electrode at any one given temperature. Even more surprising was the realization that sinusoidal signals as large as several volts peak-to-peak may be imposed across the pH probe without changing the average D.C. potential (i.e., the D.C. potential averaged over one cycle of the imposed sine wave) at the millivolt level, which is the level necessary for making accurate pH measurement.

Those acquainted with the state of the art known that pH electrodes are subject to polarization and it has been believed that imposition of such large low frequency signals would result in erroneous average D.C. potential outputs. A discovery that leads to the present invenion is that it is, in fact, feasible to simultaneously measure the average D.C. potential of a pH electrode while applying an A.C. potential to it for the purpose of measuring its electrical resistance. It should be noted that for this method to work it is necessary that the electrical resistance of the membrane be high compared to the resistance of other elements present, especially to the resistance of the solution path between the glass electrode and the reference electrode. In fact, the electrical resistance of the membrane of a pH electrode is usually many times that of the solution path.

The invention, accordingly, comprises the method, device, products, and processes of the present disclosure, together with their parts, steps, and interrelationships, the scope of which will be indicated in the appended claims.

BRIEF DESCRIPTION OF THE DRAWINGS

For a fuller understanding of the nature and objects of the present invention, reference is made to the following specification which is to be read in reference to the accompanying drawing, wherein:

FIG. 1 is a combination block-circuit diagram of the improved apparatus for obtaining temperature corrected readings of ion levels and readings of solution temperature in accordance with and embodying the present invention.

DETAILED DESCRIPTION OF THE PREFERRED EMBODIMENT

While the invention will be described in connection with a preferred embodiment, it will be understood that the invention is not limited to this particular embodiment. On the contrary, the invention is intended to cover all alternatives, modifications, and equivalents as may be included within the spirit and scope of the invention as defined by the appended claims.

The preferred embodiment of the invention shown in combination block and circuit diagram (FIG. 1) is an improved pH meter. Reference character 10 indicates a glass membrane pH probe immersed in solution 13. The probe contains reference electrode 11 and sensing electrode 12. Reference electrode 11 and sensing electrode 12 can be in separate housings, if desired.

In the present invention, amplifier 14 is a high input impedance amplifier of the type conventionally employed in pH meters. Calibration voltage 16 (a variable voltage D.C. source) is used to null out differences in assymetry potential and other potential differences between sensing electrode 12 and reference electrode 11. Calibration voltage 16 is used as in typical pH meters for calibration or standardization. Signal source 18 is a sine wave generator preferably in the frequency range of approximately one to twenty Hertz. While higher frequencies may be used, a relatively low frequency is chosen so that the electrical resistance of the pH probe 10 can more easily be distinguished from its shunt capacitive reactance. Other waveforms, of course, may be used, but a sine wave is preferred.

Signal generator 18 is coupled to probe 10 through capacitor 20, which is a low leakage type capacitor, typically of glass construction, with a capacitive value both large enough (for example, 100-1000 pF) to effectively couple the A.C. signal to probe 10 and small enough to provide a short charging time constant for the potential developed by the probe.

Amplifier 14 produces output 15 that is proportional to the average D.C. voltage of probe 10 (and related to the pH of the test solution, but not yet corrected for solution temperature) and the A.C. voltage induced across probe 10.

Peak A.C. detector circuitry 24 produces at output 25 a D.C. potential proportional to the amplitude of the A.C. potential across probe 10. Output 25 appears at input 32 of log amplifier 30.

The A.C. current flowing through probe 10 produces a voltage having two components in resistor 22: an in-phase resistive component and an out-of-phase reactive component. Resistor 22 typically has a value of the order of magnitude of 50 megohms. Output 27 of amplifier 26 is proportional to the voltage across resistor 22. Output 27 drives phase sensitive demodulator circuitry 28 using the phase information contained in the A.C. signal found at output 15. Output 29 is a D.C. voltage proportional to the resistive component of the A.C. current flowing through pH probe 10 (the reactive component having been rejected). Output 29 of phase sensitive demodulator circuitry 28, appears at input 33 of log amplifier 30.

Log amplifier 30 takes the log of output 25 (log V) and subtracts from it the log of output 29 (log I) to give an output proportional to log R, that is, log amplifier 30 produces a voltage proportional to the resistance of pH probe 10.

Log R is scaled (or normalized) in scaling circuitry 36 to account for the fact that various probes differ in resistance at any given temperature. The reciprocal of the scaled value of log R appears as output 40 of linearizing amplifier 38. (Over a temperature range of any 50 degrees between 0 and 100 degrees Celsius this linearizing is not absolutely necessary since 1/T varies approximately in proportion to T.) Thus, output 40 is a voltage proportional to the temperature of the test solution. Appropriately scaled, it may be displayed directly as a temperature reading or used to produce a temperature corrected pH reading, or both.

A.C. rejection circuitry 42 removes the A.C. component of signal 15 so that a D.C. potential appears at output 44 that is proportional to the D.C. potential developed by probe 10 minus the potential of calibration voltage 16. Output 44 is related to the pH of solution 13, but must be scaled for temperature in accordance with the Nernst equation to provide a pH reading.

Ratiometric analog-to-digital converter 50 has as inputs output 40, related to the temperature of the test solution, and output 44, related to the solution pH. Analog-to-digital converter 50 is coupled to display 54 (for example, an LED or LCD display, well known in the art) to provide direct digital readout of solution pH corrected for solution temperature. It is obvious that the inputs to converter 50 may be switched so that the display may also provide direct digital readout of solution temperature.

An improved and combined temperature and temperature-compensated pH measurement apparatus and method for incorporation in a direct readout pH meter that satisfies the objects and advantages set forth above has now been described. A method that results in the display in digital form of temperature-compensated pH readings and test solution temperatures without the need for special temperature probes has also been described. Only one probe need be placed in a test solution to operate the improved combined temperature and temperature-compensated pH sensing apparatus of the present invention. Consequently, the test solution volume may be much smaller than heretofore possible, an important consideration in instances where only very small volumes of test solutions may be available. Further, the improved pH and temperature measurement apparatus of the invention described above eliminates the need to place two probes in a test solution to measure its pH with accuracy.

While the preferred embodiment of the invention has been described as a method and apparatus for obtaining temperature-corrected pH readings, it is obvious that the invention may be used with other ion sensitive probes to obtain temperature corrected ion readings. A glass membrane sodium electrode, for example, can be used and temperature-corrected values for sodium ion can be obtained.

Those skilled in the art, following the teachings contained herein, will recognize other combinations and arrangements of parts, components, and circuits which can be used to practice this invention. Accordingly, it is intended that all matters described in the foregoing specification or shown in the accompanying drawings be interpreted in an illustrative and not in a limiting sense.

What is claimed is:

1. Improved ion measurement apparatus comprising:
   (a) ion probe for measuring the ion level of a solution;
   (b) means for measuring the D.C. potential across said ion probe;
   (c) means for measuring said ion probe's electrical resistance;
   (d) electronic means for determining from the said two measuring means the ion level of said solution corrected for the temperature thereof.

2. The improved ion measurement apparatus of claim 1 wherein said means for measuring said ion probe's electrical resistance include means for applying an A.C. signal across said ion probe.

3. The improved ion measurement apparatus of claim 1 wherein said electronic means include means for deriving the log of said ion probe's electrical resistance.

4. The improved ion measurement apparatus of claim 1 wherein said electronic means include means for deriving the reciprocal of the log of said ion probe's electrical resistance.

5. The improved ion measurement apparatus of claim 1 wherein said ion probe includes a glass membrane electrode.

6. The improved ion measurement apparatus of claim 1 wherein said ion probe is a pH probe.

7. The improved ion measurement apparatus of claim 1 wherein said ion probe includes a sodium electrode.

8. The improved ion measurement apparatus of claim 1 wherein said electronic means include means for reading said solution temperature directly.

9. A method for effecting ion measurement corrected for temperature comprising:
   (a) placing an ion probe in a solution;
   (b) measuring the electrical resistance of, and the D.C. potential across, said probe; and
   (c) determining from said two measurements the ion level of said solution corrected for the temperature thereof.

10. The method of claim 9 wherein said measuring the electrical resistance of, and the D.C. potential across, said probe is done contemporaneously.

11. The method of claim 9 wherein said probe includes a glass membrane electrode.

12. The method of claim 9 wherein said probe includes a sodium electrode.

13. The method of claim 9 wherein said probe is a pH probe.

14. A method for effecting ion measurement corrected for temperature comprising:
   (a) placing an ion probe in a solution;
   (b) inducing an A.C. signal across said probe;
   (c) measuring the A.C. resistance of, and the D.C. potential across, said probe;
   (d) electronically determining from said two measurements the ion level of said solution corrected for the temperature thereof.

15. A method for effecting ion measurement corrected for temperature comprising:
   (a) placing an ion probe in a solution;
   (b) inducing an A.C. signal across said probe;
   (c) measuring the A.C. resistance of, and the D.C. potential across, said probe;
   (d) electronically determining from said measured A.C. resistance the log thereof; and
   (e) electronically determining from said measured D.C. potential and said log of said measured A.C. resistance the ion level of said solution corrected for the temperature thereof.

16. A method for effecting ion measurement corrected for temperature comprising:

(a) placing an ion probe in a solution;
(b) inducing an A.C. signal across said probe;
(c) measuring the A.C. resistance of, and the D.C. potential across, said probe;
(d) electronically determining from said measured A.C. resistance the reciprocal of the log thereof; and
(e) electronically determining from said measured D.C. potential and said reciprocal of the log of said measured A.C. resistance the ion level of said solution corrected for the temperature thereof.

17. The method of claim 16 wherein said ion probe is a glass membrane pH probe.

* * * * *